(12) United States Patent
Risk, Jr. et al.

(10) Patent No.: US 6,755,807 B2
(45) Date of Patent: Jun. 29, 2004

(54) WOUND TREATMENT APPARATUS

(75) Inventors: James Robert Risk, Jr., Milan, IN (US); Robert Petrosenko, Batesville, IN (US); Alan Wayne Henley, Summerville, SC (US); Ronald Leslie Sanderson, Charleston, SC (US)

(73) Assignee: Hill-Rom Services, Inc., Batesville, IN (US)

(*) Notice: Subject to any disclaimer, the term of this patent is extended or adjusted under 35 U.S.C. 154(b) by 519 days.

(21) Appl. No.: 09/725,666

(22) Filed: Nov. 29, 2000

(65) Prior Publication Data

US 2002/0161317 A1 Oct. 31, 2002

Related U.S. Application Data

(60) Provisional application No. 60/167,753, filed on Nov. 29, 1999.

(51) Int. Cl.[7] ........................... A61M 1/00; A61F 13/00
(52) U.S. Cl. ....................................... 604/319; 604/305
(58) Field of Search ................................ 604/305–308, 604/319–323, 35, 118–121, 259, 315–316, 540–544, 902; 606/131

(56) References Cited

U.S. PATENT DOCUMENTS

| | | | |
|---|---|---|---|
| 774,529 A | 11/1904 | Nieschang | |
| 1,000,001 A | 8/1911 | Holz | |
| 1,355,846 A | 10/1920 | Rannells | |
| 1,385,346 A | 7/1921 | Taylor | |
| 1,936,129 A | 11/1933 | Fisk | |
| 2,195,771 A | 4/1940 | Estler | |
| 3,026,874 A | 3/1962 | Stevens | |
| 3,367,332 A | 2/1968 | Groves | |
| 3,382,867 A | 5/1968 | Reaves | |
| 3,610,238 A | 10/1971 | Rich | |
| 3,874,387 A | 4/1975 | Barbieri | |
| 4,080,970 A | 3/1978 | Miller | |
| 4,112,947 A | 9/1978 | Nehring | |
| 4,139,004 A | 2/1979 | Gonzalez, Jr. | |
| 4,149,541 A | 4/1979 | Gammons et al. | |
| 4,224,941 A | 9/1980 | Stivala | |
| 4,250,882 A | 2/1981 | Adair | |
| 4,275,721 A | 6/1981 | Olson | |
| 4,373,519 A | 2/1983 | Errede et al. | |
| 4,382,441 A | 5/1983 | Svedman | |
| 4,457,755 A | 7/1984 | Wilson | |
| 4,465,062 A | 8/1984 | Versaggi et al. | |
| 4,525,166 A | 6/1985 | Leclerc | |

(List continued on next page.)

FOREIGN PATENT DOCUMENTS

| | | | |
|---|---|---|---|
| DE | 0 880 953 A2 | 2/1998 | |
| EP | 0 853 950  * | 8/1995 | ............ A61M/1/00 |
| EP | 0 777 504 B1 | 10/1998 | |
| GB | 1 549 756 | 3/1978 | |
| SU | 587941 | 1/1978 | |
| SU | 1268175 A1 | 11/1986 | |

(List continued on next page.)

OTHER PUBLICATIONS

Davydov, et al., Vestn. Khir., Sep. 1988—"Vacuum Therapy in the Treatment of Acute Suppurative Diseases of Soft Tissues and Suppurative Wounds"—(English Translation by R. McElroy Translation Co., Austin, Texas).

Davydov, et al., Khirurgiia, Jun. 1990—"Pathogenic Mechanism of the Effect of Vacuum Therapy on the Course of the Wound Process" (English translation by R. McElroy Translation Co., Austin, Texas).

(List continued on next page.)

Primary Examiner—John J. Calvert
Assistant Examiner—Linh Truong
(74) Attorney, Agent, or Firm—Barnes & Thornburg

(57) ABSTRACT

A control system for use with a vacuum bandage over a wound includes a vacuum pump, a waste canister operably coupled to the pump, and a fluid source. The canister is coupled to the bandage such that, when a vacuum is applied to the canister, the vacuum is applied to the bandage. The fluid source is coupled to the bandage to selectively introduce fluid into the wound.

16 Claims, 10 Drawing Sheets

U.S. PATENT DOCUMENTS

| | | | |
|---|---|---|---|
| 4,540,412 A | 9/1985 | Van Overloop | |
| 4,569,674 A | 2/1986 | Phillips et al. | |
| 4,573,965 A | 3/1986 | Russo | |
| 4,605,399 A | 8/1986 | Weston et al. | |
| 4,608,041 A | 8/1986 | Nielsen | |
| 4,624,656 A | 11/1986 | Clark et al. | |
| 4,655,754 A | 4/1987 | Richmond et al. | |
| 4,661,093 A | 4/1987 | Beck et al. | |
| 4,717,332 A | 1/1988 | Clemens et al. | |
| 4,743,232 A | 5/1988 | Kruger | |
| 4,759,354 A | 7/1988 | Quarfoot | |
| 4,820,265 A | 4/1989 | DeSatnick et al. | |
| 4,820,284 A | 4/1989 | Hauri | |
| 4,834,110 A | 5/1989 | Richard | |
| 4,872,450 A | 10/1989 | Austad | |
| 4,906,240 A | 3/1990 | Reed et al. | |
| 4,917,112 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,969,881 A | 11/1990 | Viesturs | |
| 4,988,336 A | 1/1991 | Kohn | |
| 5,034,003 A | 7/1991 | Denance | |
| 5,086,764 A | 2/1992 | Gilman | |
| 5,100,396 A | 3/1992 | Zamierowski | |
| 5,106,362 A | 4/1992 | Gilman | |
| 5,149,331 A | 9/1992 | Ferdman et al. | |
| 5,176,502 A * | 1/1993 | Sanderson et al. | 417/18 |
| 5,228,431 A | 7/1993 | Giarretto | |
| 5,261,893 A | 11/1993 | Zamierowski | |
| 5,298,015 A | 3/1994 | Komatsuzaki et al. | |
| 5,358,494 A | 10/1994 | Svedman | |
| 5,527,293 A | 6/1996 | Zamierowski | |
| 5,578,022 A | 11/1996 | Scherson et al. | |
| 5,636,643 A | 6/1997 | Argenta et al. | |
| 5,645,081 A | 7/1997 | Argenta et al. | |
| 5,735,833 A | 4/1998 | Olson | |
| 5,817,145 A | 10/1998 | Augustine et al. | |
| 5,928,174 A | 7/1999 | Gibbins | |
| 5,947,914 A | 9/1999 | Augustine | |
| 5,954,680 A | 9/1999 | Augustine | |
| 5,961,480 A | 10/1999 | Augustine | |
| 5,964,721 A | 10/1999 | Augustine | |
| 5,964,723 A | 10/1999 | Augustine | |
| 5,986,163 A | 11/1999 | Augustine | |
| 6,010,527 A | 1/2000 | Augustine et al. | |
| 6,398,767 B1 * | 6/2002 | Fleischmann | 604/313 |

FOREIGN PATENT DOCUMENTS

| | | |
|---|---|---|
| WO | WO 90/11795 | 10/1990 |
| WO | WO 91/00718 | 1/1991 |
| WO | WO 92/19313 | 11/1992 |
| WO | WO 92/20299 | 11/1992 |
| WO | WO 93/09727 | 5/1993 |
| WO | WO 96/05873 | 2/1996 |
| WO | WO 00/07653 | 2/2000 |
| WO | WO 00/15277 | 3/2000 |
| WO | WO00/21586 | 4/2000 |
| WO | WO 00/26100 | 5/2000 |
| WO | WO 00/30567 | 6/2000 |
| WO | WO 00/32247 | 6/2000 |
| WO | WO 00/38552 | 7/2000 |
| WO | WO 00/61206 | 10/2000 |

OTHER PUBLICATIONS

Davydov, et al., Vestn. Khir., Nov. 1986—Vacuum Therapy in the Treatment of Suppurative Lactation Mastitis (English translation by R. McElroy Translation Co., Austin, Texas).

Davydov, et al., Vestin. Khir., Oct. 1988—"Bacteriological and Cytological Evaluation of the Vacuum Therapy of Suppurative Wounds" (English translation by R. McElroy Translation Co., Austin, Texas).

Davydov, et al., Vestn. Khir., Mar. 1990—"Basis of the Use of Forced Early Secondary Suture in the Treatment of Suppurative Wounds" (English translation by R. McElroy Translation Co., Austin, Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Venerol., Aug. 1965—"Vacuum Therapy of Some Skin Diseases" (English translation by R. McElroy Translation Co., Austin, Texas).

Jeter et al., Chronic Wound Care: 27: pp. 240–246—"Managing Draining Wounds and Fistulae: New and Established Methods".

Mulder, et al., Wound Healing Publication 1991—"Clinicians' Pocket Guide to Chronic Wound Repair".

Valenta, AIN Apr. 1994; pp. 44–45—"Using the Vacuum Dressing Alternative for Difficult Wounds".

Wolthuis, et al., Physiological Reviews Jul. 1974; vol. 54, No. 3, pp. 566–595—"Physiological Effects of Locally Applied Reduced Pressure in Man".

Fleischmann–WundForum Spezial IHA 1994; pp. 54–55—"Vacuum Sealing for Treatment of Problematical Wounds" (English translation provided).

Bucalo, et al., Wound Repair and Regeneration; Jul.–Sep. 1993; pp. 181–186—"Inhibition of Cell Proliferation by Chronic Wound Fluid".

Olenius, et al., Plastic and Reconstructive Surgery Feb. 1993; pp. 213–215—"Mitotic Activity in Expanded Human Skin".

Viljanto, et al., Br. J. Surg. 1976; vol. 63: pp. 427–430—"Local Hyperalimentation of Open Wounds".

Dunlop, et al., Br. J. Surg. May, 1990; vol. 77; pp. 562–563—"Vacuum Drainage of Groin Wounds after Vascular Surgery: A Controlled Trial".

Comment–Dunlop et al., Apr. 1991, pp. 505–506 on "Vacuum Drainage of Groin Wounds after Vascular Surgery".

Landis, et al., Alternate Suction and Pressure, pp. 925–961—"The Effects of Alternate Suction and Pressure on Blood Flow to the Lower Extremities".

Morykwas, et al., Extracellular Matric and Healing 1993, pp. 800, 1993—"Use of Negative Pressure to Increase the Rate of Granulation Tissue Formation in Chronic Open Wounds".

Svedman, et al., Annals of Plastic Surgery Aug. 1986; vol. 17, No. 2: pp. 125–133—"A Dressing System Providing Fluid Supply and Suction Drainage Used for Continuous or Intermittent Irrigation".

Schneider, et al., Plastic and Reconstructive Surgery Sep. 1998, pp. 1195–1198—"A New and Reliable Method of Securing Skin Grafts to the Difficult Recipient Bed".

Morykwas, et al., www.sma.org/soa/jsoawt97—Nonsurgical Modalities to Enhance Healing and Care of Soft Tissue Wounds.

Chariker, et al., Contemporary Surgery Jun. 1989; vol. 34: pp. 59–63—"Effective Management of Incisional and Cutaneous Fistulae with Closed Suction Wound Drainage".

Tittel, Eingag und Annahme des Manuskripts, Jan. 7, 1987, pp. 104–107—"New Standards in Postoperative Wound Drainage".

Genecov, et al., Annals of Plastic Surgery Mar. 1998, vol. 40, No. 3: pp. 219–225—"A Controlled Sub–atmospheric Pressure Dressing Increases the Rate of Skin Graft Donor Site Reepithelialization".

Morykwas, et al., Annals of Plastic Surgery Jun. 1997; vol. 38, No. 6—"Vacuum–Assisted Closure: A New Method for Wound Control and Treatment: Animal Studies and Basic Foundation".

Argenta, et al., Annals of Plastic Surgery Jun. 1997; vol. 38, No. 6, "Vacuum–Assisted Closure: A New Method for Wound Control and Treatment: Clinical Experience".

Patent Application and Drawings—"Method of Treating Tissue Damage and Apparatus for Same" consisting of 28 pages.

Patent Application and Drawings—"The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499–502—"A New Dressing of Wound Healing and Flap Survival by a New Negative Pressure Device".

Medical Industry Week—article "KCI Offers New Treatment for Non–Healing Wounds".

Nakayama, et al., Plast. Reconstr. Surg. Dec. 1990; vol. 86 No. 6 pp. 1216–1219—"A New Method for the Dressing of Free Skin Grafts".

Sames, Br. Med. J., Nov. 5, 1977; vol. 2, No. 6096: 1123—"Sealing of Wounds with Vacuum Drainage".

Fleishmann, et al., Unfallchirurg, 1993; 96:488–492—"Vacuum Sealing for Treatment of Soft Tissue Injury in Open Fractures" (English translation of the Summary provided).

Teder, et al., J. of Invest. Surg. 1990; vol. 3: pp. 399–407—"Continuous Wound Irrigation in the Pig".

Wood, et al., Br. J. of Surg. 1977; vol. 64: pp. 554–557—"Foam Elastomer Dressing in the Management of Open Granulating Wounds: Experience with 250 Patients".

Neumann, et al., J. of Biomed. Materials Research 1981; vol. 15: pp. 9–18—"Gelatin–Based Sprayable Foam as a Skin Susbstitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta. Physiol. Scand. 1989; vol. 136: pp. 403–409—"Transmission of Externally Applied Negative Pressure to the Underlying Tissue. A Study on the Upper Arm of Man".

Brochure—Aeros—Instavac Aspirator.

Brochure—Pleur–Evac Adult–Pediatric—Non–Metered Disposable "3–Bottle" Unit, A–4000.

Brochure—Hiblow Air Pump.

Brochure—Aeros—Care–E–Vac.

Brochure—Aeros—Aeros—MoblvacII.

Bochure/Instruction Manual—Creative Medical Laboratories, Inc.—TUGS (Transportable Universal Gradient Suction) System.

Brochure—Wells Johnson Company—Point 5 Aspirator.

Brochure—Microtek Heritage, Inc.—The Wound Evac ET, Closed Wound Suction System.

Brochure—KCI—The V.A.C. (Vacuum Assisted Closure).

Brochure—Augustine Medical, Warm–Up Active Wound Therapy Wound Covers, 1999.

Brochure—Series 55—Emerson Post–Operative Suction Pumps.

Brochure—Emerson Transport Suction Unit.

* cited by examiner

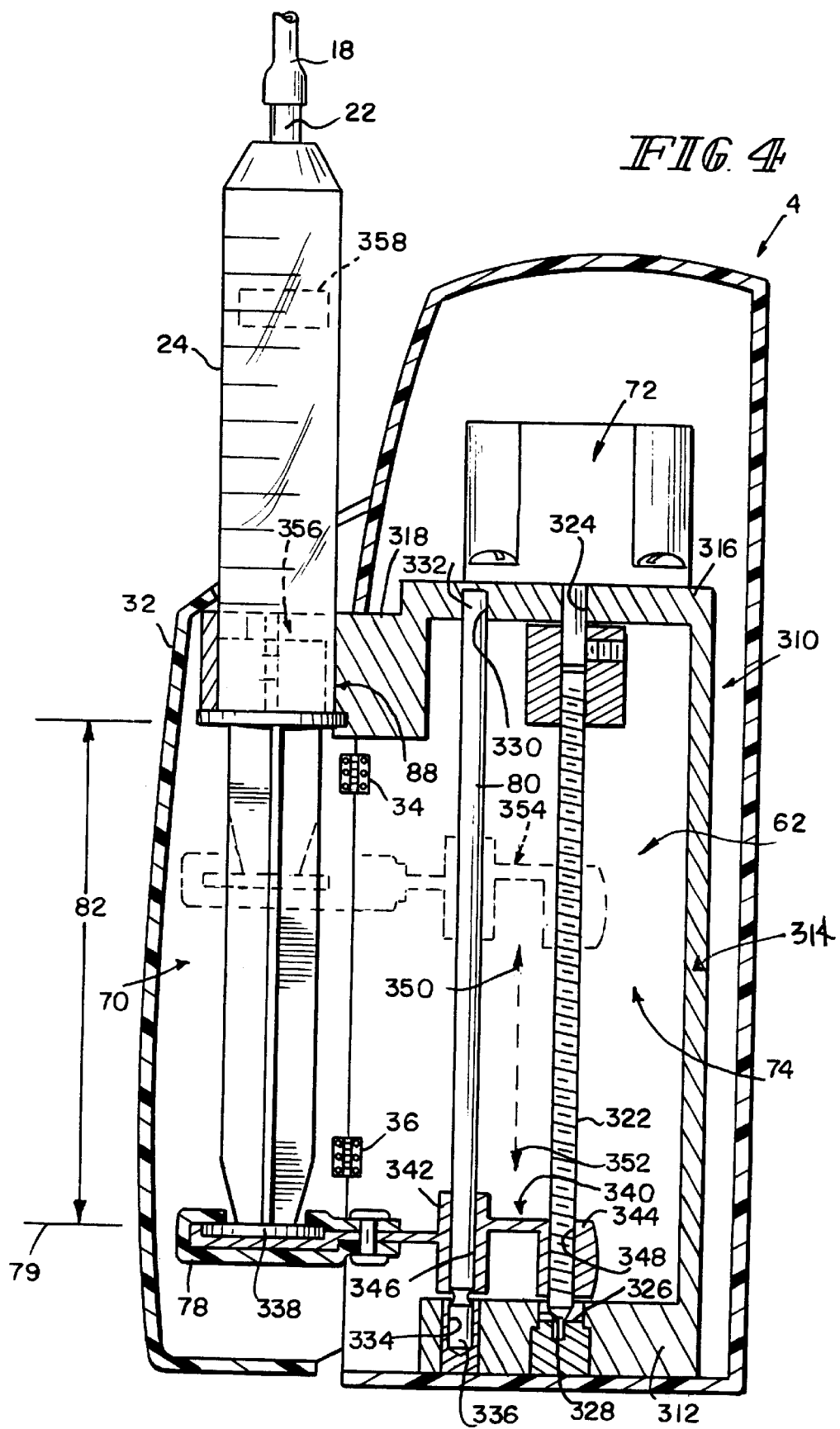

WOUND TREATMENT APPARATUS

RELATED APPLICATIONS

The present disclosure is based upon U.S. Provisional Application Serial No. 60/167,753, filed on Nov. 29, 1999, the complete disclosure of which is hereby expressly incorporated by reference.

TECHNICAL FIELD

The present invention relates to wound treatment apparatus for use with vacuum bandages of the type that dispenses fluid to a wound and draws fluid away from the wound.

BACKGROUND AND SUMMARY

Medical professionals, such as nurses and doctors, routinely treat patients having surface wounds of varying size, shape, and severity. It is known that controlling the topical atmosphere adjacent a wound can enhance the healing process. For example, by applying medicinal agents or even water over a wound, dirt and bacteria are either killed or washed away, thereby promoting healing. In addition, applying a negative pressure or vacuum to a wound draws out exudate, which might contain dirt and bacteria, from the wound to further promote healing.

Conventional treatment of a surface wound involves placement of a packing or dressing material, such as cotton, gauze, or other bandage-like material directly in contact with the patient's wound. Often there is a need to change the dressing material frequently because it becomes saturated with exudate discharged from the wound. Some dressings include an apparatus attached thereto for applying a vacuum through the bandage to the wound to draw exudate and promote healing. These bandages, however, need to be changed often so medicinal fluids can be applied to the wound, or because the bandage is soiled.

Changing vacuum bandages, however, poses several potential problems for the patient. Inadvertent contact with sensitive tissue within and adjacent the wound may cause significant discomfort to the patient, as well as further trauma to the wound. In addition, exposing the wound to the open atmosphere can increase the chance of infection.

Medical caregivers and patients both would benefit from an apparatus that would dispense fluid into a wound, and draw the fluid and exudate from the wound without having to change the bandage covering the wound. It would be a further benefit to the caregiver if the apparatus provided a collection unit to store the discharged material, and that unit could be disposed of in a sanitary manner. In addition, because it is well known that patients often suffer from more than one wound, patients would benefit from an apparatus that can treat two wounds simultaneously and independently.

Accordingly, an illustrative embodiment provides a control system for use with a bandage of the type which covers a wound and within which a vacuum is formed in a space above the wound. The control system comprises a vacuum pump, a waste canister, a fluid source and a drive. The waste canister is operably coupled to the pump and the drive is associated with the fluid source. The canister is coupled to the bandage such that, when a vacuum is applied to the canister, the vacuum is applied to the bandage. The fluid source is coupled to the bandage such that, when the drive is energized, fluid is introduced into the wound.

Further illustrative embodiments comprise a syringe having a plunger coupled to the control system as the fluid source. An illustrative drive comprises a motor and a plunger interface movable by the motor to drive the plunger. Illustratively, the motor is operatively coupled to a lead screw to rotate the lead screw. The lead screw is operatively coupled to the plunger interface to move the plunger interface to drive the plunger and expel the fluid. In other illustrative embodiments, the fluid source is a container or bag containing fluid and held at an elevated position to provide irrigation through the control system to the bandage.

Additional embodiments may include the waste canister being a disposable waste canister.

Another illustrative embodiment further provides a control system that comprises two such vacuum pumps, two such waste canisters, two such fluid sources and two such drivers for use with two such bandages for dual vacuum therapy and irrigation systems. The controller provides independent operation of the dual systems.

Another illustrative embodiment of the control system provides a housing, a controller, a pair of vacuum pumps, a pair of syringe mounts, a pair of syringe drives, and a pair of waste canister mounts, a pair of waste canisters and a pair of syringes. The controller is configured to provide independent operation of each of the vacuum pumps. Each of the canisters is removably attached to one of the canister mounts, and each is in communication with a bandage and one of the vacuum pumps. Each of the syringes is removably attached to one of the syringe mounts, and in communication with the bandage.

Further illustrative embodiments of the control system include a pair of sensors configured to determine the amount of fluid in each of the syringes. Another pair of sensors is provided each configured to determine the position of the plunger of one of the syringes.

Another illustrative embodiment of the control system provides a connector for each of the waste canisters, allowing operation of the controller when at least one of the waste canisters is coupled to one of the waste canister mounts. Each connector is configured to suspend operation of the controller when at least one of the waste canisters is removed from one of the waste canister mounts. Illustrative embodiments further provide a pair of valves. Each valve connects one of the vacuum pumps to one of the waste canisters. Each valve is adjustable to establish the level of vacuum in each of the canisters. A pair of vacuum regulators is also provided, each coupled to one of the valves. Each of the regulators is configured to define a maximum level of vacuum. Each of the regulators also comprises an air intake for supplying additional air to one of the pumps. A pair of transducers is provided each coupled between one of the valves and waste canisters for measuring vacuum.

Additional features and advantages of the apparatus will become apparent to those skilled in the art upon consideration of the following detailed descriptions exemplifying the best mode of carrying out the apparatus as presently perceived.

BRIEF DESCRIPTION OF THE DRAWINGS

The illustrative apparatus will be described hereinafter with reference to the attached drawings, which are given as non-limiting examples only, in which:

FIG. 4 is a side cross-sectional view of the wound treatment apparatus along the lines A—A of FIG. 1;

Corresponding reference characters indicate corresponding parts throughout the several views. The exemplification set out herein illustrates several embodiments of the apparatus, and such exemplification is not to be construed as limiting the scope of the apparatus in any manner.

DETAILED DESCRIPTION OF THE DRAWINGS

Figure 1:
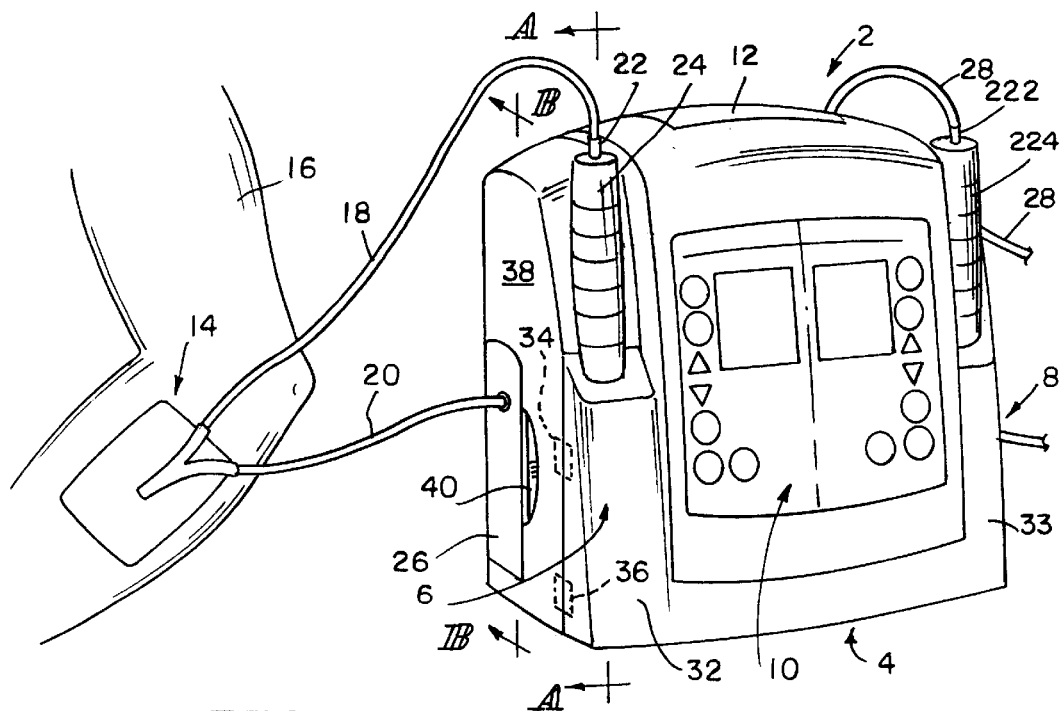
FIG. 1 is a perspective view of a wound treatment apparatus coupled to a bandage attached to a patient.

An embodiment of wound treatment apparatus 2 is shown in FIG. 1. Wound treatment apparatus 2 comprises a central unit housing 4, having wound treatment systems 6, 8 appended to each side of housing 4. A user interface 10 is shown positioned between each treatment system 6, 8. Central unit housing 4 is configured to be a portable unit allowing a caregiver to move housing 4 to wherever the patient is located and to close proximity to the wound or wounds. Housing 4 is shown having a handle portion 12 to assist the caregiver in moving housing 4. FIG. 1 also shows wound treatment system 6 coupled to a bandage 14 attached to a patient's leg 16. Dispensing and evacuating tubes 18, 20 are coupled to both bandage 14 and system 6. Specifically, dispensing tube 18 is coupled to a luer-lok port 22 extending from syringe 24. Syringe 24 is filled with a fluid, typically saline, that empties through tube 18 and into bandage 14, and ultimately onto a wound 300 positioned under bandage 14. (See also FIG. 9.) After contacting wound 300, the fluid and exudate from wound 300 are drawn from bandage 14 through evacuating tube 20 and into a waste canister 26 where it is collected. It is contemplated that the canister 26 can be discarded when filled and replaced with a new canister 26.

Apparatus 2 comprises a second system 8 on the opposite side of housing 4 from system 6. This configuration allows two wounds to be treated simultaneously with separate bandages, yet, under the control of a single housing 4. Second bandage 15, as part of system 8, is coupled to dispensing and evacuating tubes 28, 30, respectively, to perform the same functions as described for system 6. (See FIG. 2.) User interface 10 is provided to allow the caregiver to control either or both systems 6, 8, to dispense fluid from either or both syringes 24, 224, and to evacuate from either or both bandages 14, 15. It is contemplated that each wound treatment system 6, 8 will work independent of each other, thus, allowing the caregiver flexibility to apply an appropriate and, yet, possibly different level of treatment to each wound.

The arrangement of systems 6, 8 relative to user interface 10 on housing 4 allows convenient interaction between systems 6, 8 and the caregiver. For example, syringes 24, 224 are conveniently positioned on opposite sides of user interface 10. Each syringe is partially covered by doors 32, 33 on the front of housing 4. Each door 32, 33 swings outwardly about hinges 34, 36, allowing syringes 24, 224 to be removed and replaced. Similarly, waste canisters 26, 27 are each positioned in a cavity 9 provided on each side of housing 4. (See FIG. 7.) Each canister 26, 27 includes a grip portion 40 for convenient removal and replacement. Canisters 26, 27 are illustratively secured into each cavity by a friction fit. (See FIG. 6.) It is appreciated, however, that syringes 24, 224 can be secured to other locations on housing 4.

The portability of apparatus 2 allows a caregiver to position it near the patient in preparation for treatment wherever the patient is located. To prepare apparatus 2 for treatment, the caregiver secures syringes 24, 224, which contain fluid, to apparatus 2 in a manner described in greater detail below. The caregiver then couples tube 18 to port 22 and bandage 14, and tube 20 to bandage 14 and waste canister 26, for treatment of one wound. The caregiver then couples tube 28 to port 222 and bandage 15, and tube 30 to bandage 15 and waste canister 27, for treatment of a second wound. (See also FIG. 2.) The caregiver, through the use of user interface 10 can treat the patient by selectively irrigating the wounds with fluid and drawing exudate and the fluid from the wounds.

Figure 2:
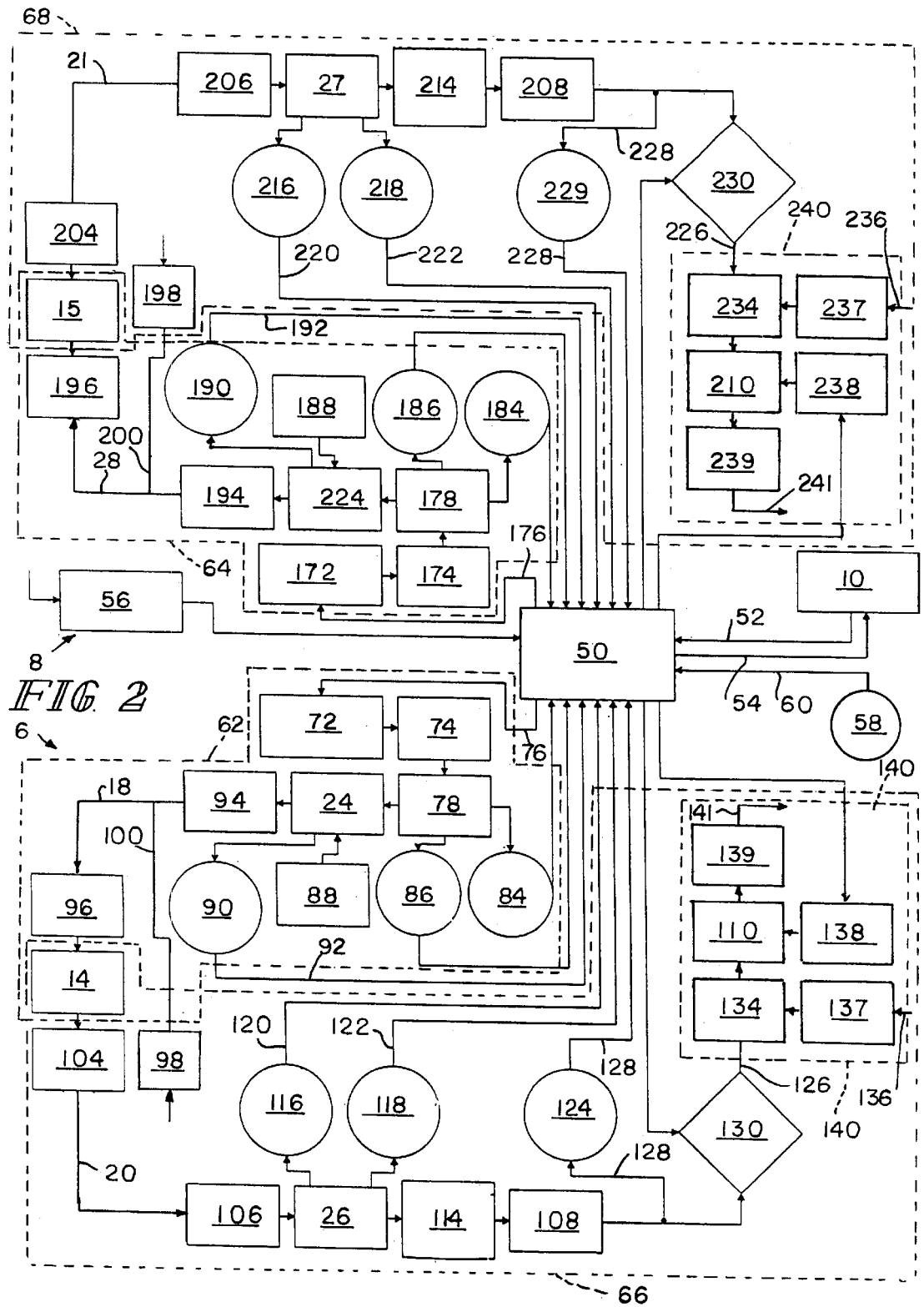
FIG. 2 is a block diagram of the wound treatment apparatus of FIG. 1.

A diagram depicting how wound apparatus 2 operates is shown in FIG. 2. A controller 50 is provided in housing 4 and is an electronic control unit that controls apparatus 2. Controller 50 receives user input from and provides feedback to user interface 10 through lines 52, 54, respectively. It is contemplated that controller 50 will process information from both systems 6, 8, and provide appropriate and independent input to each system. Controller 50 also monitors the status of all various sensors, and provides input for the valves and motors, as discussed in further detail herein. Illustratively, user interface 10 is composed of a conventional graphic liquid crystal display (LCD) and a membrane switch panel.

A power supply 56 provides power to controller 50 and all the attendant systems in housing 4. Power supply 56 can be a conventional external wall socket supply (not shown), or be a battery pack supply (also not shown), or even be variations of both (e.g., a wall socket supply with a battery pack supply).

Illustratively, power supply 56 is a medical grade power supply providing an output of about 65-watts and a voltage of about 12VDC. It is contemplated that the power supply can be configured for 120V/60 Hz or 220–240V/50 Hz depending on whether housing 4 is used in America or Europe. Illustratively, the battery power provides the device with power to operate for about 60 minutes without connection to an external power source. It is further contemplated that the batteries can be rechargeable, and store energy when the device is connected to an external wall socket.

An attitude sensor 58 is provided in communication with controller 50 through line 60. Attitude sensor 58 is, illustratively, a tilt switch which provides feedback to controller 50. If the switch is, illustratively, in the closed position, controller 50 will continue to operate, but if the switch opens, controller will shut systems 6, 8 down. For example, sensor 58 disables systems 6, 8 if housing 4 tilts at or greater than a predetermined amount, such as 45° from vertical in any direction.

It is contemplated that controller 50, user interface 10, power supply 56, and attitude sensor 58 are all common to and all operate with both systems 6, 8. Each system 6, 8 further comprises fluid dispensing and vacuum evacuating sub-systems 62, 64 and 66, 68. Fluid dispensing sub-system 62 comprises a syringe 24 having a plunger 70. (See also FIG. 4.) Syringe 24 is, illustratively, a standard 60-ml medical syringe utilizing a luer-lok port 22. Plunger 70 is a conventional plunger that extends into syringe 24 to dispense fluid through luer-lok port 22. A syringe drive motor 72 is, illustratively, a 12VDC brushless electric motor or stepper motor configured to provide rotational energy to a syringe drive 74. (See FIG. 4.) When a signal is sent from controller 50 along line 76 to syringe drive motor 72, motor 72 applies torque and angular velocity to syringe drive 74 which is, illustratively, a power screw 322. (See also FIG. 4.) Power screw 322 translates rotational movement of the syringe drive motor 72 into translational movement. The drive has a guide 80 to limit a plunger interface 78 to motion along one axis. In the illustrated embodiment, syringe drive motor 72 provides about 5.25 inches (13.3 cm) of travel of plunger interface 78, indicated by reference numeral 82, to evacuate the fluid contained in syringe 24. (See also FIG. 4.) Furthermore, syringe drive motor 72 and syringe drive 74, as a system, provide about 27 pounds of linear force at a velocity of 1.45 inches (3.7 cm) per second to the plunger interface 78. The resulting force created by the fluid exiting syringe 24 creates, illustratively, 4-PSIG to 6-PSIG positive pressure at wound 300.

A syringe home sensor 84 receives information from plunger interface 78, and provides feedback to controller 50 when syringe capture mechanism 88 reaches its home position 79. A syringe fall travel sensor 86 determines when syringe 24 is fully evacuated by sensing when plunger interface 78 has reached fall travel. After sensor 86 has been activated, controller 50 resets plunger interface 78 to home position 79 once syringe 24 is removed.

Syringe capture mechanism 88 holds syringe 24 in place when the caregiver places syringe 24 in apparatus 2. (See also FIG. 4.) Capture mechanism 88 is also configured to allow the caregiver to release syringe 24 from apparatus 2 when it is empty. Capture mechanism 88 further includes a syringe sensor 90 that provides feedback to controller 50 through line 92 when syringe 24 is properly held in capture mechanism 88. Controller 50 prevents system 6 from operating if sensor 90 does not detect syringe 24 being properly held in capture mechanism 88.

Connectors 94, 96 are provided at opposed ends of dispensing tube 18. Either one or both connectors 94, 96, when closed, block flow from syringe 24 to bandage 14. Such connectors 94, 96 allow the patient to be disconnected from apparatus 2 without having to remove bandage 14 or even shut apparatus 2 down.

A manual port 98 is also attached to dispensing tube 18 by an auxiliary tube 100. Port 98 permits the caregiver to attach a dispensing container to the system to manually dispense fluid into bandage 14. It is appreciated, however, that port 98 is configured to be closed while no syringe is attached to maintain a closed system.

The syringe and drive are illustrated as one approach for providing a fluid source and a drive for irrigating a wound bed. It will be appreciated that containers other than syringes may be operated by a drive to expel irrigation fluid toward a wound surface. For example, any type of container of fluid may be squeezed or reduced in volume by a drive mechanism to expel fluid. Also, as discussed in connection with FIG. 8, a container may be held at an elevated position to provide head pressure for irrigation fluid.

Connectors 104, 106, similar to connectors 94, 96, are provided at opposed ends of evacuating tube 20. Either one or both connectors 104, 106, when closed, block flow from bandage 14 to waste canister 26. Such connectors 104, 106 also allow the patient to be disconnected from apparatus 2 without having to remove bandage 14 or having to shut down apparatus 2.

Waste canister sensors 116, 118 are engaged when waste container 26 is properly seated in apparatus 2. This prevents apparatus 2 from operating without canister 26 seated properly in apparatus 2. As depicted in FIG. 2, both sensors 116, 118 provide feedback to controller 50 through lines 120, 122, confirming to the caregiver that canister 26 is seated properly in apparatus 2.

In the illustrated embodiment, waste canister 26 is a disposable unit that "snaps into" side portion 38 of housing 4. (See also FIGS. 1 and 6.) Illustratively, canister 26 includes a window (not shown) to allow monitoring of the fluids. Illustratively, the fluid capacity of canister 26 is about 500-ml.

The illustrated embodiment of waste canister 26 further includes a hydrophobic filter 108 that is in communication with both evacuating tube 20 and vacuum pump 110. (See also FIG. 6.) Such filter 108 is configured to allow air, but not liquid, to pass. Accordingly, as fluid is drawn into canister 26, fluid is deposited into waste canister 26 while the vacuum continues through filter 108 and pump 110. Illustratively, filter 108 is a 0.2-micron hydrophobic bacteria filter fixed into rear wall 407 of canister 26. (See FIG. 6.) Hydrophobic filter 108 also serves as a canister full mechanism 114 or valve that shuts off the vacuum supply to the canister 26 when the fluid level exceeds the "full" level 420. Because hydrophobic filter 108 prevents fluid from passing, once fluid covers filter 108, vacuum is prevented from passing as well. The absence of any vacuum in the system will cause the system to shut down.

Figure 5:
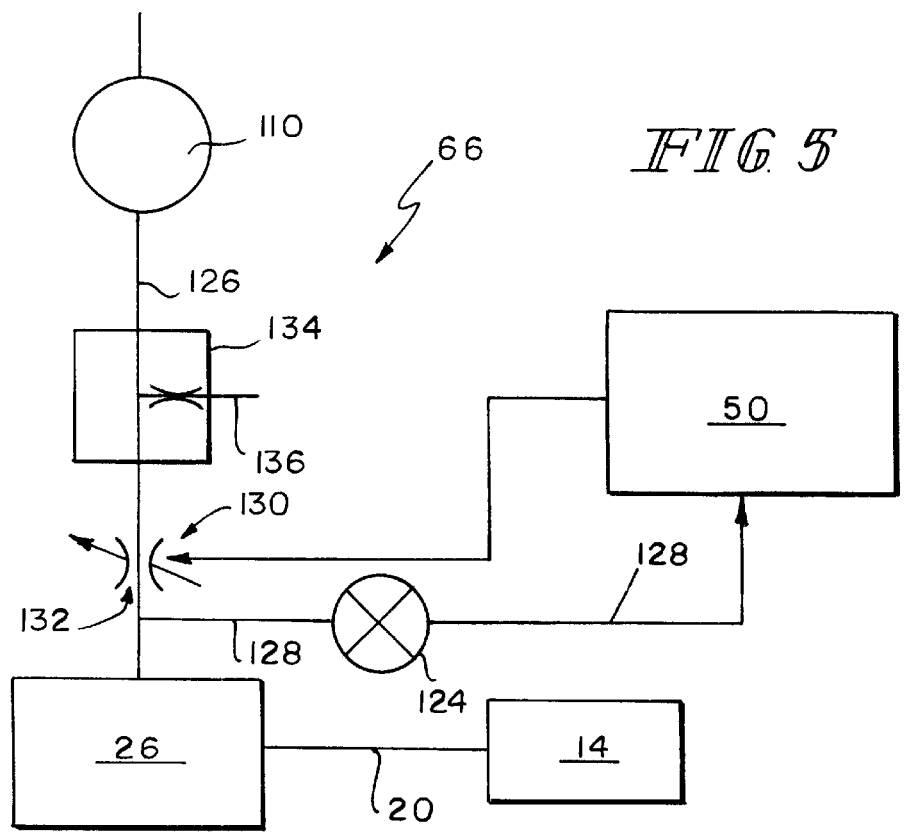
FIG. 5 is a schematic block diagram of the vacuum evacuating subsystem of the wound treatment apparatus of FIG. 1.

Vacuum pump 110 creates the negative pressure that is present through canister 26. For monitoring and controlling such negative pressure, the vacuum is present through several devices, including a vacuum pressure transducer 124. Transducer 124 is coupled to line 128, extending from canister 26. (See FIG. 5.) Transducer 124 measures the negative pressure that is present through canister 26. Transducer 124 then provides feedback to controller 50 through line 128. Controller 50 monitors the negative pressure by comparing the measured value from transducer 124 with the caregiver-defined value entered into controller 50 through user interface 10.

A proportional valve 130 is connected to line 126, through which the negative pressure is present, and which comprises a flow orifice 132. (See also FIG. 5.) Flow orifice 132 selectively dilates or constricts, thereby controlling the negative pressure level through sub-system 66. Specifically, controller 50 provides a signal input to proportional valve 130 based on the level of the vacuum pressure determined from feedback of transducer 124 and comparing that level to the caregiver-defined level. Orifice 132 then dilates or constricts, as necessary, to produce the appropriate level of negative pressure. Illustratively, proportional valve 130 is fully constricted or closed when receiving no signal from controller 50, and dilates or opens to allow an illustrative maximum of two liters per minute at 250-mmHg (4.83-PSIG) vacuum when the proper signal from controller 50 is applied.

A vacuum regulator 134 is provided in line 126 between proportional valve 130 and pump 110 as a mechanical limit control for pump 110. Regulator 134 mechanically establishes a maximum level of negative pressure that is present in the system. Thus, vacuum pump 110 will not physically be able to draw a vacuum from bandage 14 beyond the maximum pressure. Illustratively, such maximum negative pressure or vacuum is 250-mmHg (4.83-PSIG). In addition, when proportional valve 130, pursuant to a signal from controller 50, creates a negative pressure less than the maximum negative pressure level, a port 136, coupled to regulator 134, opens so that pump 110 can draw more air to maintain a sufficient flow through pump 110, to prevent it from becoming damaged. A first air filter 137 is illustratively associated with port 136, between port 136 and pump 110, to filter particulates from the air prior to reaching pump 110. Illustratively, filter 137 is constructed of glass microfibers with a filtration rating of 25 microns. A second filter 139 is associated with pump 110 and an outlet 141. Filter 139 serves as an exhaust muffler for the air evacuated from pump 110.

Vacuum pump 110 is, illustratively, a diaphragm-type compressor that flows about two liters per minute at 250-mmHg (4.83-PSIG) vacuum. Illustratively, vacuum pump 110 is mounted on the end of a single 12VDC brushless motor 138 to drive the pump. It is appreciated, however, that pump 110 can be of any other configuration, and mounted in any manner, so long as it draws a desired negative pressure through system 6. It is also contemplated that a vacuum pump external to the housing 4 may be a part of the control system. For example, most medical facilities have vacuum ports near where patients are treated, each of which is served by a system vacuum (suction) pump. It is contemplated, therefore, that the pump 110 in the housing 4 may be an appropriate fitting which is, in turn, connected to a facility vacuum pump to provide a vacuum source to the control system.

It is contemplated that port 136, filters 137, 139, electric motor 138, vacuum pump 110, and vacuum regulator 134 are all housed in a sound chamber 140. Illustratively, the interior of sound chamber 140 is lined with a damping foil like the 3M Company's damping foil number 2552, for example. Sound chamber 140 dampens vibration energy produced by these components, as well as assists in dissipating heat they generated.

As previously indicated, it is contemplated that controller 50, user interface 10, power supply 56, and attitude sensor 58 are common to, and operate with, both fluid dispensing and vacuum evacuating sub-systems 62, 64 and 66, 68. Providing a second independently operable set of sub-systems 64, 68 allows the caregiver to treat two wounds using a single apparatus 2. Accordingly, second fluid dispensing and evacuating sub-systems 64, 68 also shown in FIG. 2, comprise identical components as discussed regarding sub-systems 62, 66 and are labeled in a corresponding manner. For example, syringe motor drive 72 in sub-system 62 is identified as syringe motor drive 172 in sub-system 64, and a vacuum pump 110 in sub-system 66 is identified as vacuum pump 210 in sub-system 68.

Figure 3:
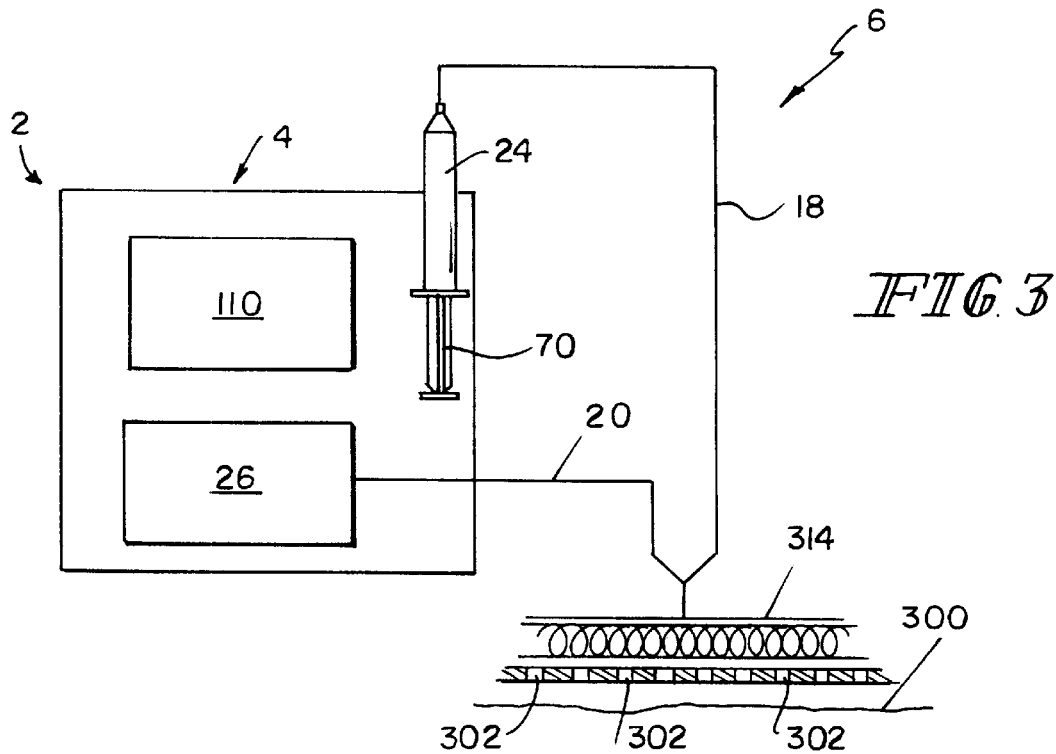
FIG. 3 is a schematic diagram of the wound treatment apparatus of FIG. 1.

A schematic diagram of a portion of wound treatment apparatus 2 is shown in FIG. 3. Each system 6 and 8 is configured to operate in the same manner. Specifically, FIG. 3 depicts the operation of system 6. Movement of plunger 70 into syringe 24 causes fluid stored in syringe 24 to exit into tube 18 and into bandage 14 where it drains through orifices 302 onto wound 300. Vacuum 110 applies a negative pressure through waste canister 26 and bandage 14. Fluid and exudate are then drawn from wound 300 out through tube 20 and into canister 26. The hydrophobic filter 108, discussed in connection with FIG. 2, allows the vacuum to pass through waste canister 26, yet, prevents any of the fluid from escaping, and depositing the fluid into pump 110.

The mechanism for moving plunger 70 into syringe 24, part of fluid dispensing sub-system 62, is shown in cross-sectional form in FIG. 4. The illustrated embodiment includes sub-system 62 positioned within housing 4. Specifically, a bracket frame 310 serves as the skeletal structure for sub-system 62. Bracket 310 includes a base portion 312 with an upwardly extending structural member 314 appending from one end thereof. A support portion 316 extends outwardly from member 314, and is superposed above base portion 312. Extending from support portion 316 is syringe bracket 318. Syringe capture mechanism 88 is formed in bracket 318, and is configured to receive syringe 24, as previously discussed. Bracket 318 and capture mechanism 88 are configured to suspend syringe 24 with luer-lok port 22 directed upwardly. It is contemplated that capture mechanism 88 secures syringe 24 to bracket 318 by other means, including being friction-fitted, or secured with clips or bolts. To move plunger 70, syringe drive 74 and plunger interface 78 are coupled to frame 310. Plunger interface 78 captures plunger 70 and provides upward linear motion to evacuate syringe 24. Interface 78 provides a release mechanism for plunger 70 to remove syringe 24 at any position in the stroke.

Syringe drive 74 comprises syringe drive motor 72 and power screw 322. Power screw 322 is disposed through an aperture 324 in support portion 316, and is rotatably coupled to motor 72. It is appreciated that motor 72 can be a stepper or electric motor, for example. The lower end 326 of power screw 322 is positioned within a bearing cavity 328 within which power screw 322 rotates. Spaced in parallel to power screw 322 is guide 80. Guide 80 is received in an aperture 330, also disposed in support portion 316 at its upper end 332, and is received in cavity 334 at its lower end 336. Plunger interface 78 is configured to receive cap 338 of plunger 70, and is coupled to a dual coupler 340. Dual coupler 340 comprises two blocks 342, 344, each having bores 346, 348 disposed, respectively, there through. In the illustrated embodiment, bore 346 has a smooth surface and is configured to receive guide 80. In contrast, bore 348 has a threaded surface and is configured to cooperate with threads on power screw 322. Coupler 340 is movable upwardly and downwardly in directions 350, 352. A hatched outline version of coupling 340, indicated by reference numeral 354, is shown depicting plunger interface 78 and plunger 70 moving upwardly in direction 350. As shown in FIG. 4, as plunger 70 is moved upwardly, head 356 is also moved upwardly, reducing the available space in syringe 24, thus, displacing any fluid in syringe 24 out of luer-lock port 22, thereby dispensing the fluid into tube 18 and into bandage 14. The movement of cap 356 is depicted by the position of cap 356 in hatched lines moved to an upper position indicated by reference numeral 358.

Figure 6:
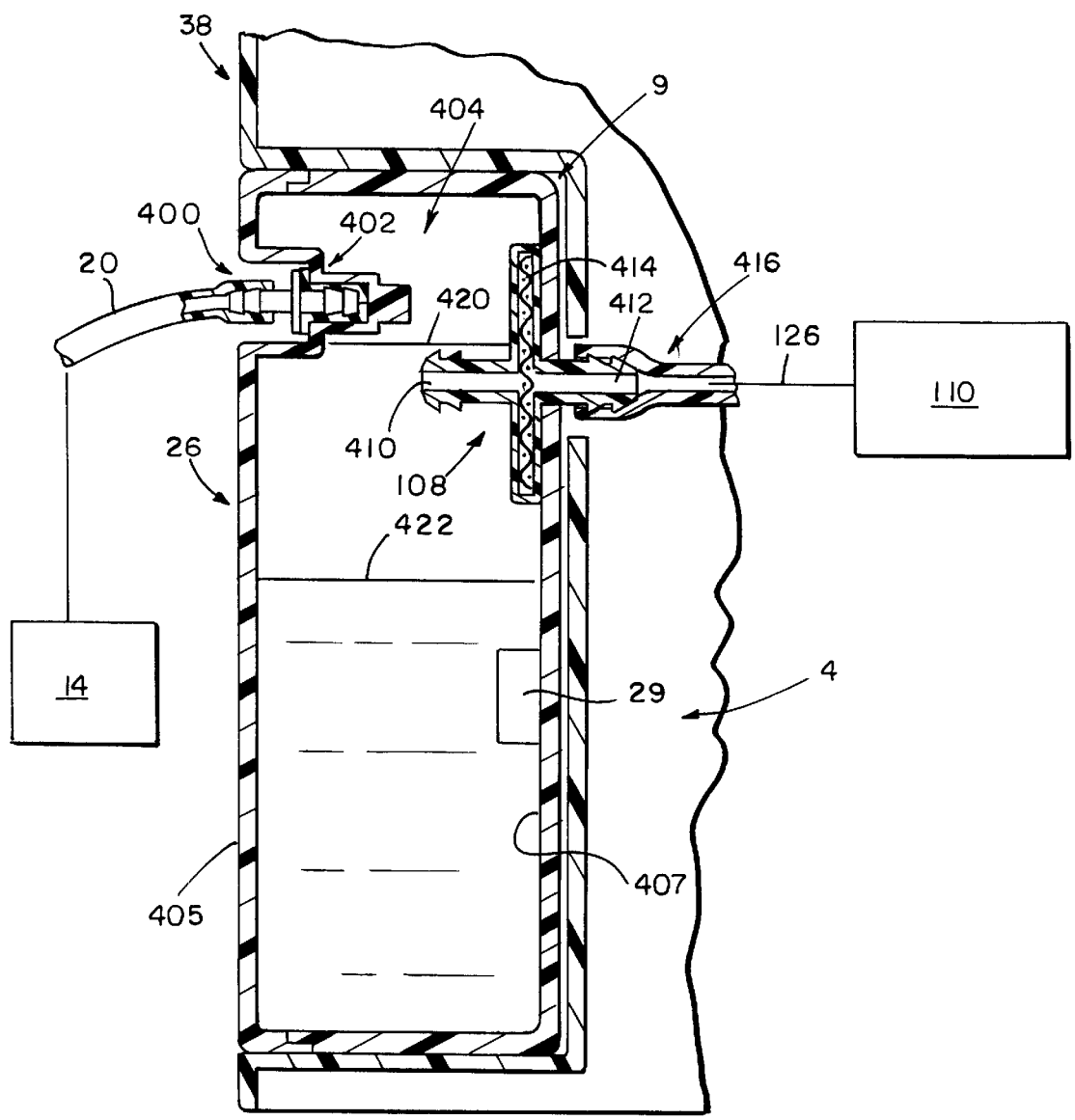
FIG. 6 is a cross-sectional view of a waste disposal canister of the wound treatment apparatus along the lines B—B of FIG. 1.

A cross-sectional view of waste canister 26 located in cavity 9 on side 38 of housing 4 is shown in FIG. 6. Tube 20 is connected to a check-valve assembly 400 coupled to recess 402 disposed in the front wall 405 of canister 26. Check valve 400 is configured to allow fluid and exudate from bandage 14 to enter canister 26 and deposit in holding space 404 within canister 26, yet prevent any fluid already in space 404 from exiting through valve 400. Check valve 400, thus prevents fluid from escaping when tube 20 is disengaged from valve 400. In addition, canister 26 can be discarded without any fluid escaping. Hydrophobic filter 108 is located on the rear wall 407 of canister 26. A liquid solidifier 29 is provided in space 404 to decease the fluidity of the exudate. This is a safety measure to lessen the chance of splashing or run-off if canister 26 (or 27) is opened or broken.

Filter 108 in canister 26 is shown having an inlet 410 provided in space 404 and an outlet 412 coupled to a connector 416 with a barrier of hydrophobic material 414 provided there between. As previously discussed, the hydrophobic material allows the vacuum to pass through inlet 410 and outlet 412, yet prevents any fluid from passing. Similar to check valve 400, hydrophobic filter 108 too prevents any fluid from escaping even when canister 26 is removed from housing 4. Outlet 412 of filter 108 is in communication with connector 416. Connector 416 is configured to receive and seal outlet 412 when canister is positioned in cavity 9. Connector 416 is in communication with line 126 and ultimately with pump 110.

In the illustrated embodiment, hydrophobic filter 108 serves as both the canister full mechanism 114 that shuts off the vacuum supply to the canister 26 when the fluid level exceeds the "full" level as indicated by reference numeral 420. When the fluid level is below inlet 410, as indicated by reference numeral 422, fluid continues to enter space 404 through valve 400. When the fluid level 420 is above inlet 410, the fluid is acting as an air block. Fluid cannot pass through filter 108, but because the fluid level is above inlet 410, air cannot pass through either. This causes a dramatic pressure drop (vacuum increase) through line 126. Vacuum pressure transducer 124 is coupled to line 126 measuring the negative pressure passing through canister 26, as previously discussed. If such a dramatic pressure drop occurs, transducer 124 will provide such data to controller 50 through line 128. Controller 50 will then know to shut the system down until the full canister is replaced with either an empty or only a partially fall canister.

Figure 8:
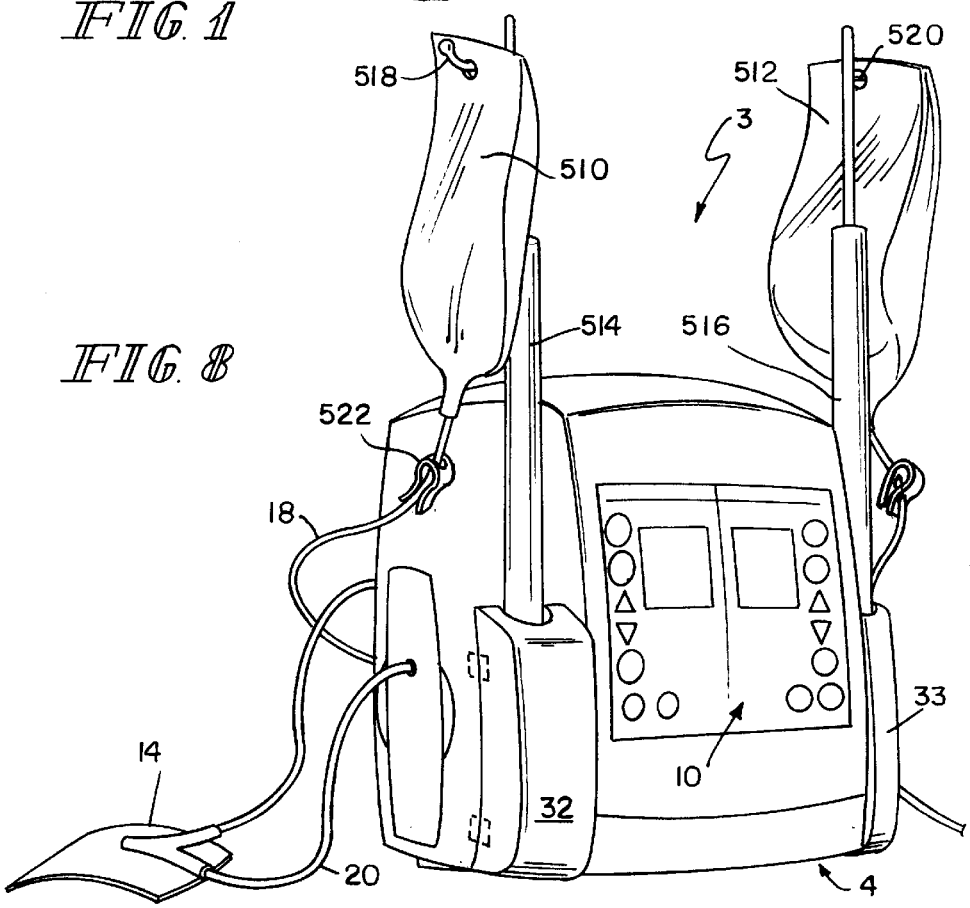
FIG. 8 is a perspective view of another embodiment of the wound treatment apparatus.

Another illustrative embodiment of a wound treatment apparatus is shown in FIG. 8 and is indicated by reference numeral 3. Apparatus 3 operates in a similar manner as apparatus 2, with the exception of the use of two "intravenousstyle" fluid bags 510, 512 suspended above housing 4 to dispense the fluid. In this illustrated embodiment, posts 514, 516 with hooks 518, 520 extend upwardly of apparatus 3 from behind doors 32, 33. It will be appreciated that the posts 514, 516 may be extensible to elevate the bags 510, 512 to selected heights to provide selected pressures for irrigation. A dispensing tube 18 extends from each bag 510, 512 at one end and couples to each bandage. Gravity assists in moving fluid through tubes 18 and into the bandages. A tube clip 522 is coupled to each tube 18 and configured to pinch and close tube allowing the caregiver to selectively prevent fluid from dispensing into bandages.

Illustrative vacuum bandage 314 of FIG. 3 is designed to provide a protective environment around wound 300. Illustratively, such bandages last for up to 7 days without having to be replaced. Bandage 314 includes rinse and drain orifices (not shown) within the body of bandage 314 that communicate with tubes 18, 20, respectively. Such orifices are illustratively 0.070-inch (0.18 cm) diameter. Vacuum evacuating sub-system 66 cooperates with bandage 314, similar to bandage 14, to draw the fluid and exudate from the surface of wound 300, and collect same into waste canister 26.

Examples of bandages 14 and 15 are shown in U.S. patent application Ser. No. 09/725,352, entitled VACUUM THERAPY AND CLEANSING DRESSING FOR WOUNDS, filed concurrently with the present disclosure on Nov. 29, 2000, and assigned to the same Assignee or Affiliated Assignee as the present disclosure, and the complete disclosure of which is hereby expressly incorporated by reference. It is further contemplated that other bandages may be used with this control system, including bandages having separate irrigation and vacuum ports. Examples of such bandages are shown in U.S. patent application Ser. No. 09/369,113, entitled WOUND TREATMENT APPARATUS, filed on Aug. 5, 1999, and assigned to the same Assignee or Affiliated Assignee as the present disclosure, and the complete disclosure of which is hereby expressly incorporated by reference.

Figure 9:
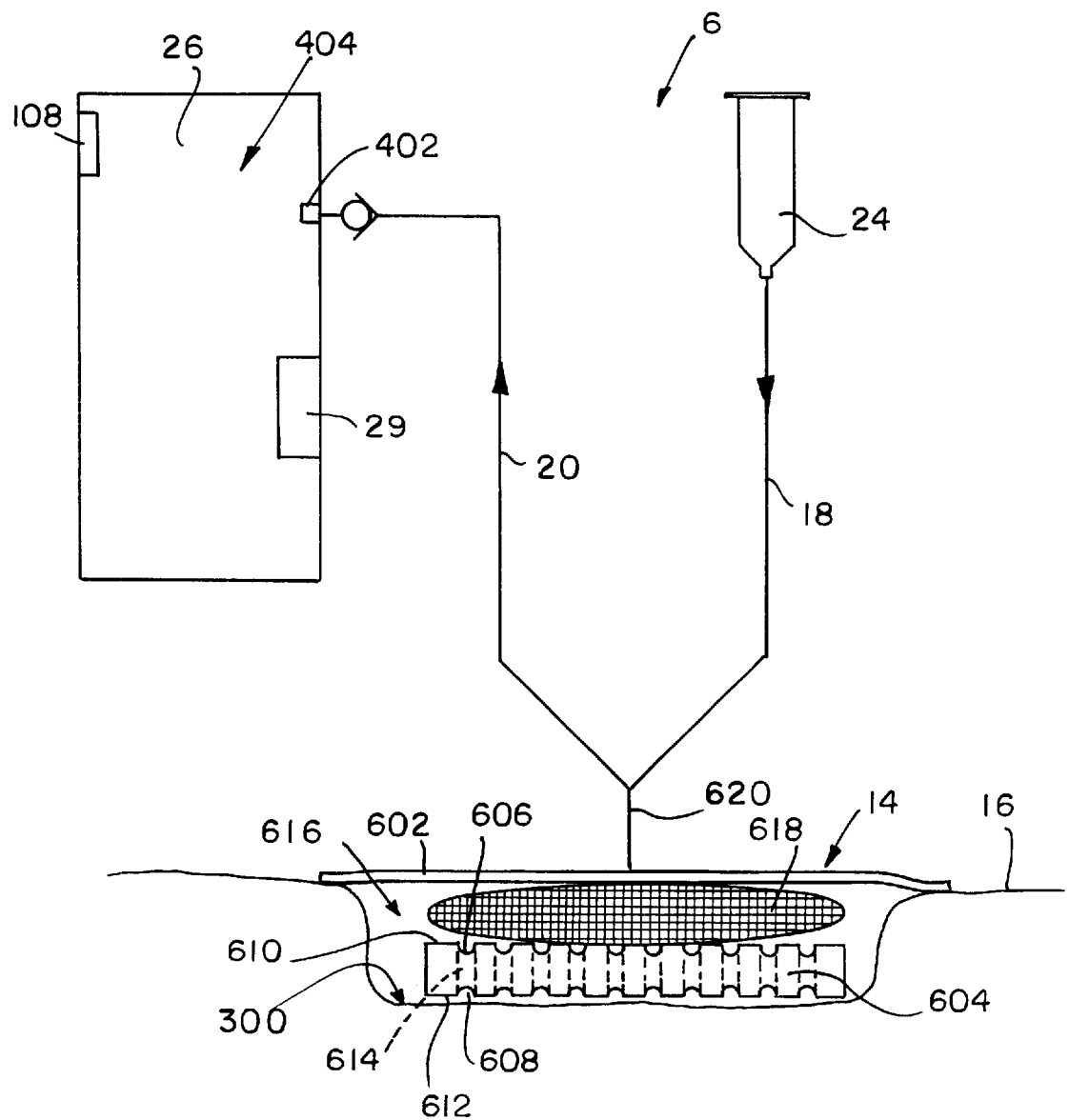
FIG. 9 is a side diagrammatic view of the vacuum bandage and portions of the wound treatment apparatus of FIG. 1.

A side diagrammatic view of bandage 14 along with a portion of system 6 is shown in FIG. 9. (See also FIG. 1.) Bandage 14 is of an illustrative type for use with apparatus 2. (Note that the bandage is not drawn to scale.) As previously discussed, bandage 14 is a vacuum bandage. Bandage 14 comprises a cover film 602, illustratively a flexible cover, that seals wound 300 about its outer perimeter. It is contemplated, however, that film 602 can be made from an occlusive or semi-occlusive material that allows water vapor to permeate there through, but otherwise protects wound 300 from the outside environment. A bandage member 604 is placed adjacent wound 300 and is configured to irrigate wound 300. In the illustrated embodiment, bandage member 604 comprises upper channels 606 and lower channels 608, each provided on opposite sides 610, 612, respectively, of bandage member 604. Each of the upper channels 606 is generally congruent with one of the lower channels 608. Channels 606 and 608 are in communication with each other via apertures 614. As shown in the illustrated embodiment, side 612 of bandage member 604 faces wound 300, and side 610 faces a porous packing 618. Packing 618 provided under film 602 to assist in providing a space 616 to facilitate the negative pressure. Packing 618 is typically a gauze material.

Illustratively, the caregiver may activate system 6, by means previously described, to draw exudate from wound 300 through channels 606, 608 and apertures 614 of bandage member 604, packing 618 and film 602, through splitter tube 620 connected to evacuating tube 20, and deposit in canister 26. The negative pressure applied to wound 300 created by pump 110 can be applied for a period of time as determined by the caregiver. After a period of drawing, the caregiver may deactivate the negative pressure. The caregiver may begin irrigating wound 300 by releasing fluid from syringe 24, through tube 18, into splitter tube 620, through film 602 and packing 618, and into bandage member 604. The fluid will travel through channels 606 deposit in apertures 614 and irrigate wound 300 by traveling through channels 608. Illustratively, the fluid will continue to irrigate wound 300 until space 616 can no longer receive any more fluid. The fluid is held in space 616 for a period of time as determined by the caregiver. After that period, pump 110 is reactivated and the fluid and exudate from wound 300 is evacuated from bandage 14 and into canister 26 by the manner previously described. This process is repeated as many times as necessary as determined by the caregiver.

In one embodiment, user interface 10 comprises a momentary switch (not shown) that selectively operates the aforementioned process. For example, the switch may be configured such that when the caregiver depresses and holds the switch, the fluid will dispense from syringe 24 into bandage 14. When the caregiver releases the switch the fluid will stop dispensing and pump 110 will activate and begin drawing the fluid and exudate. It is contemplated that the switch may be configured to delay between the vacuuming and dispensing for a period of time that is definable by the caregiver. It is also contemplated that all of the aforementioned descriptions as applied to system 6 are applicable to system 8.

The apparatus 2 is a portable, easy to use topical system that is intended to provide a protective/occlusive environment with features to facilitate the administering of standard wound care. The apparatus 2 provides for the care of two independently controlled wounds. The apparatus 2 provides negative pressure to the wound bed, and the caregiver can set the level of negative pressure. Illustratively, the negative pressure is variable from 25-mmHg to 225-mmHg at increments of 10-mmHg. The caregiver can choose between continuous, intermittent (profile), and no negative pressure modes. It will be appreciated that the apparatus 2 may be set up to provide various levels of vacuum at various times. The apparatus may be provided with the ability to pause negative pressure therapy for set durations of time. The system may be set up to provide audible alarms to remind the caregiver to reset or start a new cycle of vacuum therapy.

The apparatus 2 is intended to provide an occlusive wound healing environment. The apparatus 2 provides an active therapy unit that delivers drainage and cleansing for aggressive wound healing. It is intended, for example, for use on all pressure ulcers (Stage II through Stage IV), surgical draining wounds and leg ulcers.

Figure 7:
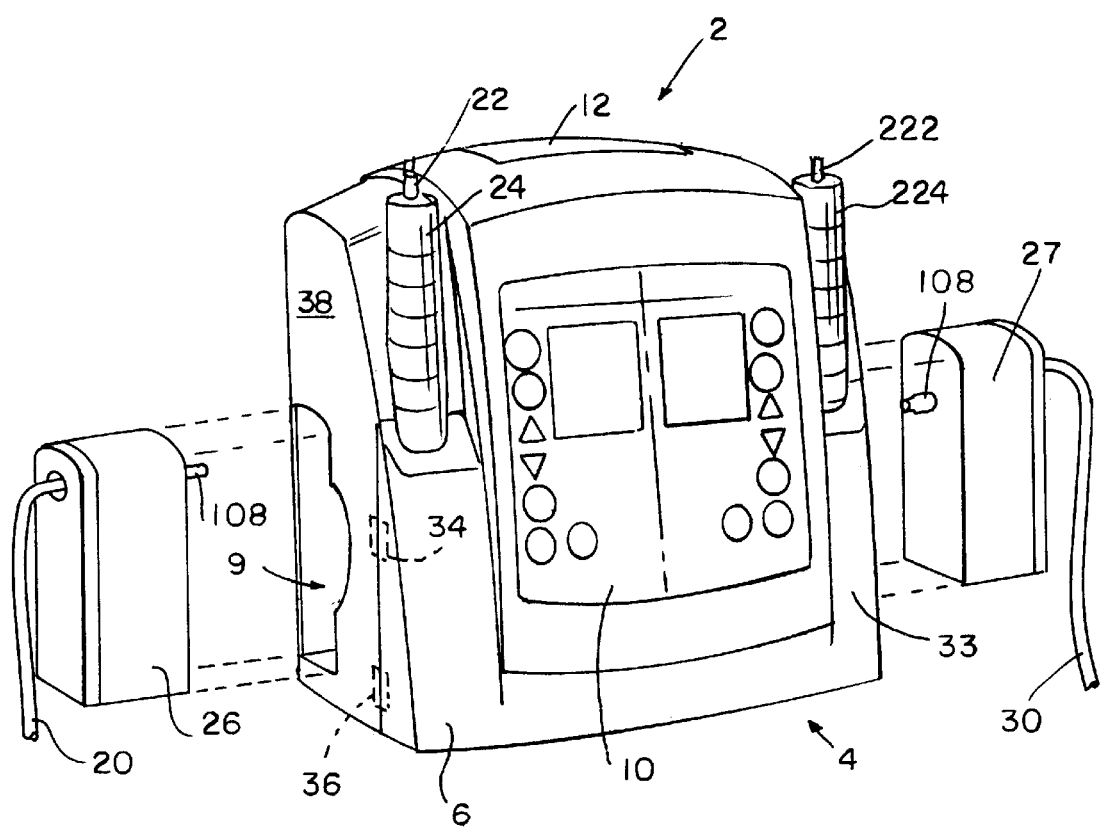
FIG. 7 is a partially exploded perspective view of the wound treatment apparatus of FIG. 1 with the waste canisters removed.
Figure 10:
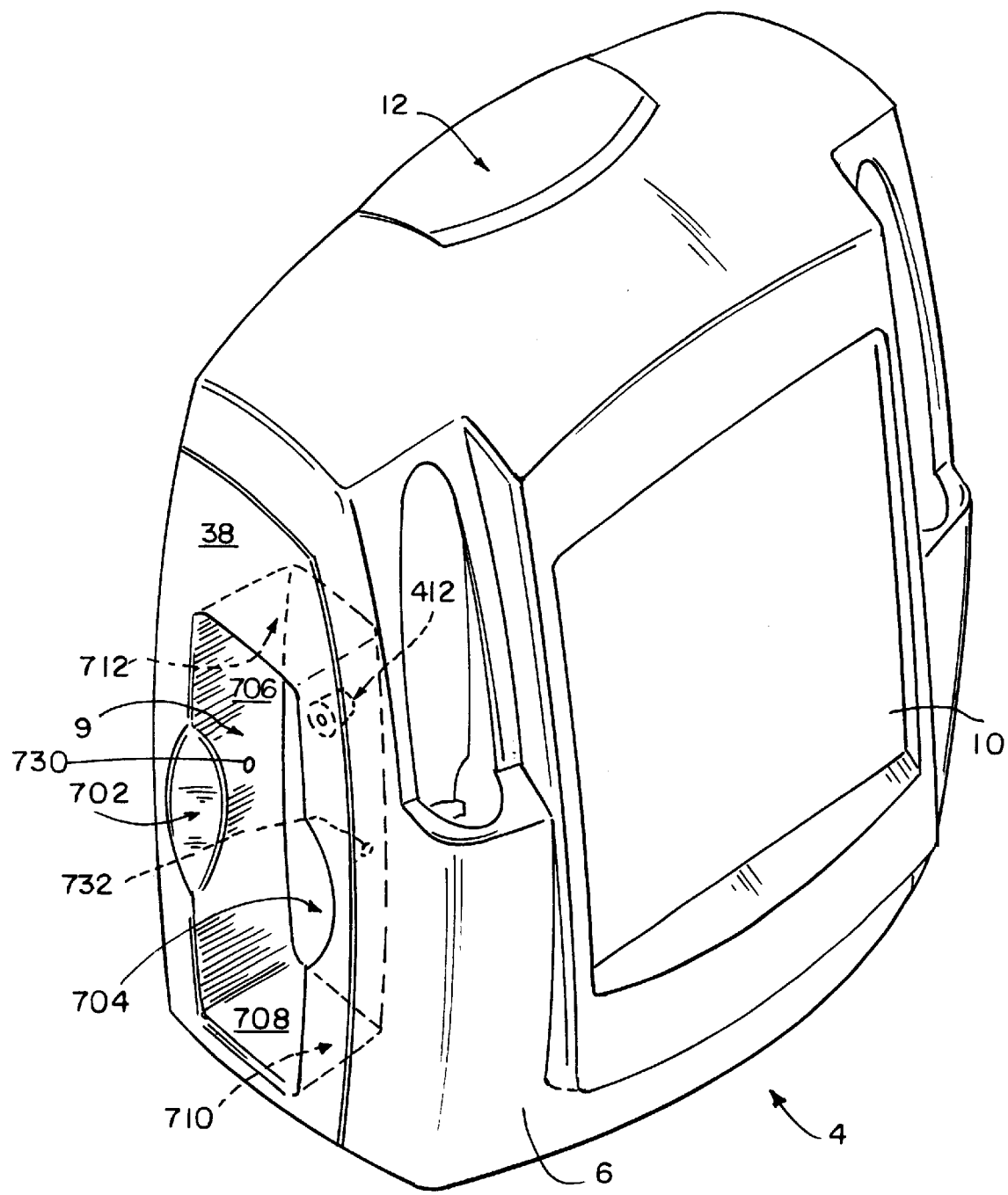
FIG. 10 is a perspective view of the wound treatment apparatus of FIG. 1 with the waste cannister removed.
Figure 11:
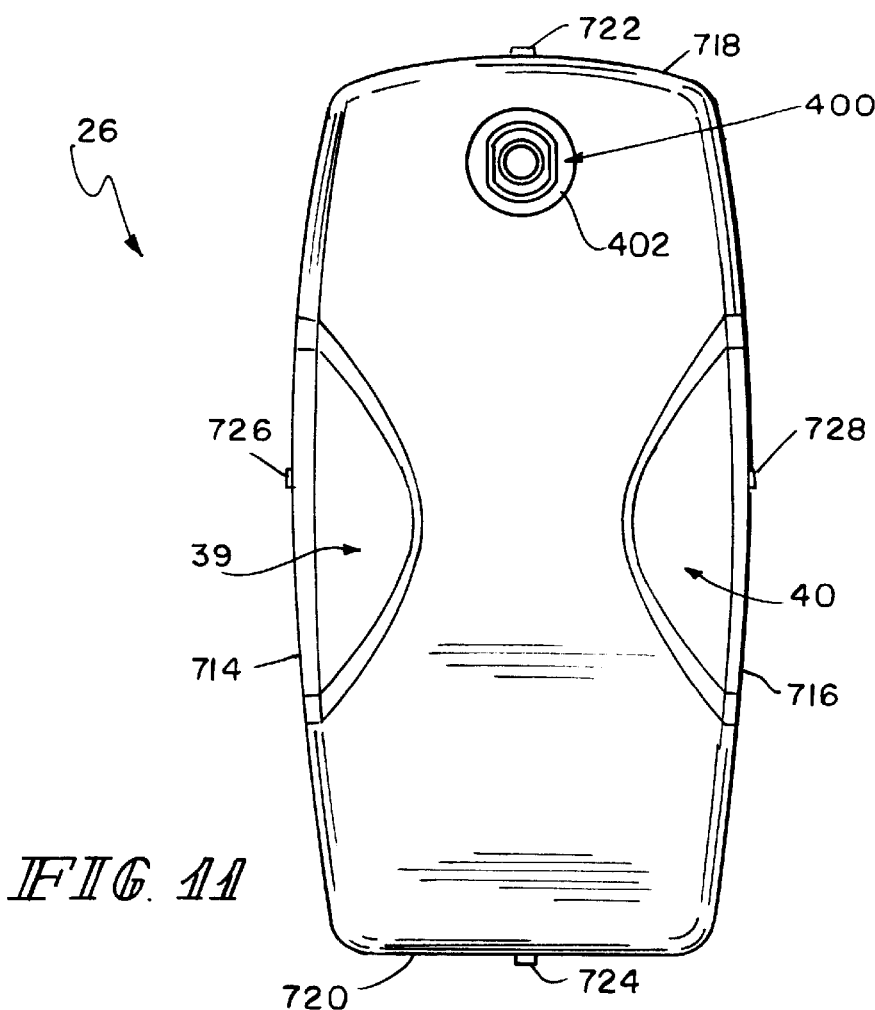
FIG. 11 is a front elevational view of a waste canister.
Figure 13:
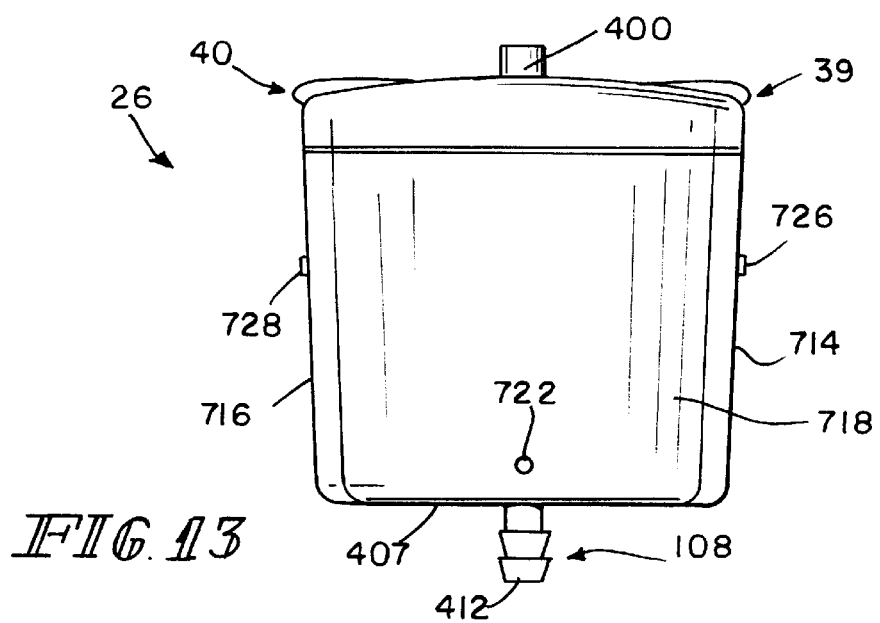
FIG. 13 is a top view of the waste canister of FIG. 11.
Figure 12:
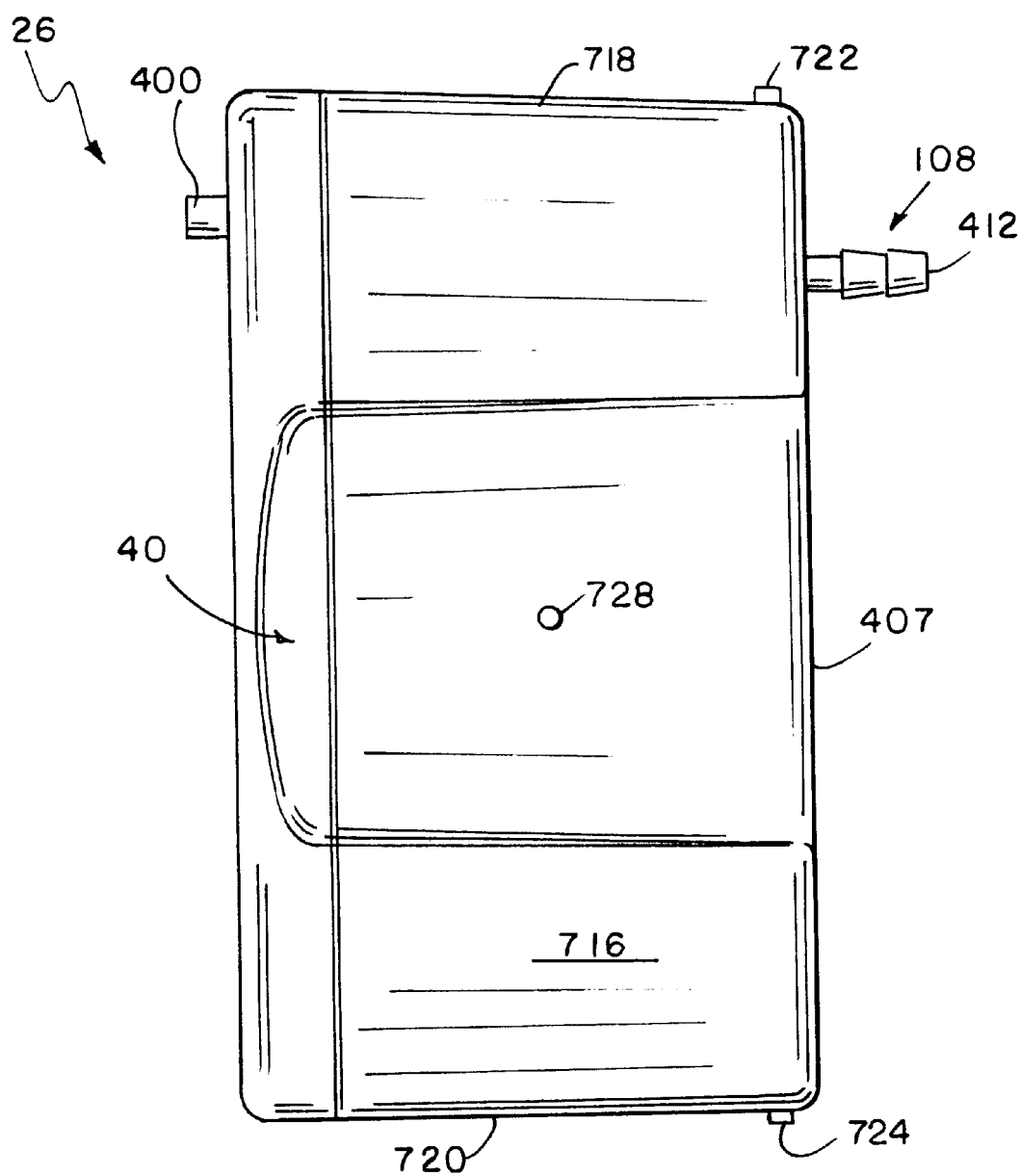
FIG. 12 is a side elevational view of the waste canister of FIG. 11.

In the illustrated embodiment, as shown in FIGS. 7 and 10, for example, canister 26 is configured to be received in cavity 9 disposed in side 38 of housing 4. As shown specifically in FIG. 10, cavity 9 comprises two pull recesses 702, 704. Such recesses 702, 704 are concave-shaped portions formed adjacent to side 38 and to side walls 706 and 710. Recesses 702, 704 are provided to allow finger clearance when the caregiver grasps grip portions 39, 40 of canister 26 to remove it from, or insert it into cavity 9. (See also FIGS. 1, 11 and 13.) Side walls 706, 710 and bottom and top walls 708, 712 define cavity 9 such that cavity 9 provides a relatively conforming receptacle for the canister 26. The walls 706, 710 and 708, 712 conform to the size and shape of the panels 714, 716, 718, 720 of canister 26. (See FIGS. 12 and 13.) Outlet 412 of filter 108 mates with connector 416 to produce an air-tight seal between port 412 and connector 416. It is further contemplated that other structures or configurations of outlet 412 and connector 416 can be used to ensure system 6 is a closed system when canister 26 is properly coupled to housing 4. It is still further contemplated that the aforementioned descriptions of canister 26 of system 6 apply equally to canister 27 of system 8.

Each of top and bottom panel 718, 720 of canister 26 includes a boss 722, 724, respectively. Each boss 722, 724 is configured to engage a sensor such as sensor 116, 118, respectively, as depicted in FIG. 2. This engagement provides a signal to controller 50 indicating that canister 26 is seated properly into cavity 9 and the vacuum therapy treatment may begin to be administered. It is contemplated that bosses 722, 724 can be mechanical sensors, optical, capacitive or other similar type sensors.

Side panels 714, 716 include buttons 726, 728 to assist the caregiver in placing canister 26 in the proper location within cavity 9. Illustratively, buttons 726, 728 are small protrusions, each extending from a side panel. Each button 726, 728 is configured to be received or "snapped" into corresponding dimples 730, 732, respectively, disposed in walls 706, 710, respectively. In the illustrated embodiment, the buttons extend from the widest point of side panels 714, 716 of canister 26.

Although the foregoing apparatus has been described, one skilled in the art can easily ascertain the essential characteristics of the apparatus, and various changes and modifications may be made to adapt the various uses and characteristics without departing from the spirit and scope of this disclosure, as described by the claims which follow.

What is claimed is:

1. Disposables, in combination with a housing, for use with a vacuum bandage of the type which covers a wound and wherein a vacuum is formed in the space above the wound, the housing including a controller, a canister mount, a syringe mount configured to hold a syringe, and the controller configured to create the vacuum in the space above the wound, the disposables comprising:

a waste canister mateable with the canister mount;

a tube set configured to be coupled to the waste canister, the syringe, and the bandage; and the tube set connecting the vacuum to the bandage through the canister.

2. The disposables of claim 1, comprising a pair of waste canisters to be mated with a pair of canister mounts for use with a pair of bandages, and the tube set to be coupled to each of the waste canisters and each of the bandages.

3. A canister, in combination with a housing, for use with a vacuum wound bandage, the housing including a control apparatus, the control apparatus connecting a vacuum to the bandage, the canister comprising:

a container having an outer wall and an inlet port, the container insertable into a cavity in the control apparatus; and wherein both the outer wall and inlet port of the container are substantially flush with an exterior wall of the housing when the container is inserted into the cavity.

4. The canister of claim 3, wherein the inlet port includes a valve to prevent fluid in the container from exiting the canister.

5. The canister of claim 4, wherein the valve is a check valve.

6. The canister of claim 3, wherein the outlet port includes a filter that prevents fluid in the container from exiting the canister.

7. The canister of claim 6, wherein the filter is a hydrophobic filter.

8. The canister of claim 3, wherein the vacuum is introduced to the bandage from the inlet port.

9. The canister of claim 6, wherein the inlet port is provided above the outlet port relative to a plane defined by the level of fluid collected in the container.

10. For use with a control apparatus providing a vacuum source and a shaped cavity having a suction port leading to the vacuum, and a bandage of the type which covers a wound and within which a vacuum, generated by the control apparatus, is formed in a space above the wound, a canister comprising:

a container configured and shaped to be inserted into the shaped cavity;

the container having an inlet port configured to be in communication with the bandage, the inlet port configured to receive fluid and exudate from the wound and deposit the fluid and exudate in the container;

the container having an outlet port positioned to engage the suction port of the control apparatus, the outlet port being configured to introduce the vacuum from the control apparatus to the container, the outlet pod including a filter that prevents fluid in the container from exiting the canister;

the inlet port being provided above the outlet port relative to a plane defined by the level of fluid collected in the container; and wherein when the level of fluid is positioned above the outlet port, the vacuum is caused to cease, indicating that the container is full.

11. The canister of claim 3, further comprising a liquid solidifier material in the container.

12. The canister of claim 9, wherein the canister is a disposable canister.

13. The canister of claim 10, wherein the outlet port communicates with a vacuum pump in the control apparatus.

14. The canister of claim 6, wherein the inlet port communicates with a tube coupled to the bandage, the tube being configured to receive fluid and exudate from the wound.

15. The canister of claim 3, in which the canister is further configured and shaped with a hand grip to selectively remove the canister from the cavity.

16. The canister of claim 3, in which the container is further configured and shaped to provide an air-tight seal between the container and the cavity.

* * * * *